(12) United States Patent
Sagstetter

(10) Patent No.: US 6,709,428 B2
(45) Date of Patent: Mar. 23, 2004

(54) NEEDLE DESIGN AND MANUFACTURING METHOD FOR MEDICAL APPLICATIONS

(75) Inventor: William E. Sagstetter, Denver, CO (US)

(73) Assignee: Baxter International, Inc., Deerfield, IL (US)

( * ) Notice: Subject to any disclaimer, the term of this patent is extended or adjusted under 35 U.S.C. 154(b) by 0 days.

(21) Appl. No.: 09/866,139

(22) Filed: May 25, 2001

(65) Prior Publication Data
US 2002/0010435 A1 Jan. 24, 2002

Related U.S. Application Data
(60) Provisional application No. 60/207,709, filed on May 26, 2000.

(51) Int. Cl.⁷ .................................................. A61M 25/00
(52) U.S. Cl. .................... 604/523; 604/264; 604/272; 604/164.07; 29/525
(58) Field of Search ............................... 604/264, 272, 604/164.07, 523; 29/525, 564.2

(56) References Cited

U.S. PATENT DOCUMENTS

| 3,648,684 | A | | 3/1972 | Barmwell et al. ............ 128/2 F |
|---|---|---|---|---|
| 3,782,383 | A | * | 1/1974 | Thompson et al. .......... 127/214 |
| 4,003,262 | A | | 1/1977 | Gerarde deceased et al. . 73/425 |
| 4,176,451 | A | | 12/1979 | McMorrow ................... 30/124 |
| 4,263,922 | A | | 4/1981 | White ........................... 128/763 |
| 4,367,749 | A | | 1/1983 | Dudley, deceased et al. . 128/637 |
| 4,392,497 | A | | 7/1983 | Ghaussy ...................... 128/637 |
| 4,413,992 | A | * | 11/1983 | Soika ........................... 604/263 |
| 4,441,951 | A | | 4/1984 | Christinger .................. 156/245 |
| 4,515,752 | A | | 5/1985 | Miramanda ................... 422/99 |
| 4,581,024 | A | | 4/1986 | Swenson ...................... 604/240 |
| 4,585,444 | A | * | 4/1986 | Harris .......................... 604/177 |
| 4,589,871 | A | * | 5/1986 | Imbert ......................... 604/240 |
| 4,617,012 | A | * | 10/1986 | Vaillancourt | |
| 4,655,764 | A | | 4/1987 | Sato ............................. 604/408 |
| 4,675,007 | A | * | 6/1987 | Terry ........................... 604/283 |
| 4,840,185 | A | | 6/1989 | Hernandez ................... 128/763 |
| 4,886,072 | A | | 12/1989 | Percarpio et al. ............ 128/763 |
| 4,950,132 | A | * | 8/1990 | Brian, Jr. et al. ............ 417/269 |
| 4,972,843 | A | | 11/1990 | Broden ........................ 128/760 |
| 4,976,925 | A | | 12/1990 | Porcher et al. .............. 422/100 |
| 5,026,355 | A | | 6/1991 | Sweeney et al. ............. 604/243 |
| 5,125,058 | A | | 6/1992 | Tenerz et al. ................ 385/66 |
| 5,151,231 | A | * | 9/1992 | Lambert et al. ............ 264/108 |

(List continued on next page.)

FOREIGN PATENT DOCUMENTS

| EP | 0350792 | 1/1990 |
|---|---|---|
| JP | 59-10349 | 1/1984 |
| JP | 4-303730 | 10/1992 |
| WO | WO 94/20216 | 9/1994 |
| WO | WO 98/36834 | 8/1998 |

OTHER PUBLICATIONS

"Directions for Using Segment Sampler™," Gamma Biologicals, Inc., Houston, TX (Nov. 1994).
Introducing the SEG–SAFE™ Segment Processor, Alpha Scientific Corp., Southeastern, PA (1995).
U.S. patent application Ser. No. 09/521,739, Sagstetter, filed Mar. 9, 2000.
U.S. patent application Ser. No. 09/549,982, Sagstetter, filed Arp. 14, 2000.

Primary Examiner—Ira S. Lazarus
Assistant Examiner—Camtu Tran Nguyen
(74) Attorney, Agent, or Firm—Michael C. Mayo; Douglas W. Swartz

(57) ABSTRACT

The present invention is directed to a novel process for inserting a cannula into a hub member. The process uses an interference or frictional fit between the bore of the hub member and the cannula's exterior surface. In this manner, adhesives are not required in the assembly of the two components.

113 Claims, 5 Drawing Sheets

U.S. PATENT DOCUMENTS

| | | | |
|---|---|---|---|
| 5,207,853 A | 5/1993 | Awazu et al. | 156/293 |
| 5,215,621 A | 6/1993 | Awazu et al. | 156/423 |
| 5,254,312 A | 10/1993 | Staebler et al. | 422/100 |
| 5,257,980 A | 11/1993 | Van Antwerp et al. | 605/282 |
| 5,286,453 A | 2/1994 | Pope | 422/100 |
| 5,313,969 A | 5/1994 | Hsieh | 128/764 |
| 5,342,325 A * | 8/1994 | Lun et al. | 604/272 |
| 5,376,003 A | 12/1994 | Rizkalla | 433/116 |
| 5,380,301 A | 1/1995 | Prichard et al. | 604/281 |
| 5,385,561 A * | 1/1995 | Cerny | 604/264 |
| 5,393,674 A | 2/1995 | Levine et al. | 436/177 |
| 5,579,661 A * | 12/1996 | Yarnell et al. | 74/473 R |
| 5,714,125 A | 2/1998 | Sagstetter | 422/102 |
| 5,746,733 A * | 5/1998 | Capaccio et al. | 604/411 |
| 5,807,347 A * | 9/1998 | Bonaldo | 604/246 |
| 5,893,842 A * | 4/1999 | Imbert | 604/110 |
| 5,910,289 A * | 6/1999 | Sagstetter | 422/102 |
| 5,921,591 A * | 7/1999 | Argent | 285/330 |
| 5,960,530 A * | 10/1999 | Kerr et al. | 29/525 |
| 6,074,612 A | 6/2000 | Sagstetter | 422/100 |
| 6,162,203 A * | 12/2000 | Haaga | 604/272 |
| 6,162,236 A * | 12/2000 | Osada | 606/185 |
| 6,488,668 B1 | 12/2002 | Prindle | 604/272 |

* cited by examiner

NEEDLE DESIGN AND MANUFACTURING METHOD FOR MEDICAL APPLICATIONS

CROSS REFERENCE TO RELATED APPLICATION

This application claims priority, under 35 U.S.C. §119(e) to U.S. Provisional Patent Application, Ser. No. 60/207,709, filed May 26, 2000, entitled "IMPROVED NEEDLE DESIGN AND MANUFACTURING METHOD FOR MEDICAL APPLICATIONS." The entire disclosure of the provisional application is considered to be part of the disclosure of the accompanying application and is hereby incorporated by reference.

FIELD OF THE INVENTION

The present application is directed generally to cannulas and specifically to the securement of the cannula to a hub member.

BACKGROUND OF THE INVENTION

To be acceptable, processes for manufacturing cannula assemblies, which include a hub and cannula, must satisfy several requirements. For example, the process must have a low incidence of damaging the point of the cannula. Second, the process must have a low incidence of plugging the hollow passageway extending the length of the cannula. Third, the hub must hold onto the needle notwithstanding a film of lubricant such as silicone located on the needle. As will be appreciated, the film of lubricant is placed on the needle to reduce the resistance of skin to puncture by the needle. Fourth, the process must provide a cannula assembly in which the minimum force required to push the cannula out of the hub is greater than forces associated with its intended use, thereby precluding disassociation of the cannula from the hub.

The standard manufacturing process for cannula assemblies to be used in medical applications typically includes numerous steps. In a first step, the blunt end of the cannula is subjected to a grit blast to provide a roughened surface. A suitable epoxy is applied to the roughened surface, and the roughened surface is then placed into a cylindrical passage in a hub. The cylindrical passage has a number of peripherally disposed channels to contain the epoxy. The narrower sections of the passage (disposed between the peripheral channels) typically have a radius larger than that of the roughened surface of the cannula. The roughened surface permits the epoxy to form a strong bond between the peripherally disposed channels of the hub passage and the roughened end of the cannula. The epoxy is than cured by a suitable process, such as by exposure to ultraviolet light, elevated temperatures (via radiant heating or induction heating), and the like. Alternatively, the epoxy can use a one stage curing process with air curing or a two stage curing process in which the epoxy is mixed with a hardener or other reactant to cause curing of the epoxy. In another process, the hub is injection molded when the roughened surface is in the mold. Further, detail on conventional manufacturing processes is contained in U.S. Pat. Nos. 4,581,024; 4,655,764; 5,026,355; 5,215,621; and 5,207,853, each of which is incorporated herein by this reference.

These processes can have a number of drawbacks. First, there can be incompatability with the epoxies used to secure the cannula to the hub and the plastic material in the hub. Second, the need to cure some adhesives using ultraviolet curing requires a hub that is substantially transparent. This requirement imposes further substantial limitations on the types of plastics that can be used to form the hub. The use of a thermal cure of the adhesive can cause physical or chemical changes of the plastic which can undesirably alter the physical characteristics (e.g., strength) of the material. In addition, all the above processes require extra time in to manufacture a cannula assembly, which significantly increases costs.

SUMMARY OF THE INVENTION

These and other problems are addressed by the method and device configurations of the present invention. Generally, the present invention includes a cannula assembly having an interference fit between the cannula and a surface of a hub member. The interference fit has sufficient strength that adhesives are not required to secure the cannula to the hub member. In some cases, the ability to manufacture a cannula assembly without using adhesives represents an approximate 50% reduction in manufacturing costs and a significantly increased capacity for a given plant size compared to conventional manufacturing processes.

In a first embodiment of the present invention, a method for manufacturing a cannula assembly including a hub member and a cannula is provided. The method includes the steps of:

(a) forming (e.g., by grit blasting) a roughened exterior surface on a portion of the cannula to yield a roughened portion of the cannula such that the roughened portion is adjacent to an unroughened or substantially smooth (e.g., non-grit blasted) portion of the exterior surface of the cannula; and (b) inserting the roughened portion of the cannula into a central bore of a hub (typically after the smooth portion is inserted into the central bore), wherein a radius of the smooth portion is substantially the same as a radius of the hub bore to form a line-to-line fit between the wall of the bore and the adjacent surface of the smooth portion of the cannula and the radius of the roughened portion is slightly larger than the bore radius to form an interference fit between the wall of the bore and the adjacent, roughened portion of the cannula. As used herein, a line-to-line fit refers to a relationship between the hub bore and adjacent portion of the cannula in which the outer diameter of the adjacent portion of the cannula is the same as or slightly less than the inner diameter of the bore, and an interference fit refers to a relationship between the hub bore and adjacent portion of the cannula in which the outer diameter of the adjacent portion of the cannula is greater than the inner diameter of the hub bore.

The cannula and hub member can take on any number of configurations. The cannula is typically elongated and can have any shape. The cannula is typically formed from a metal such as a stainless steel. The hub member can be in one or several pieces and can be of many differing shapes. A preferred hub member configuration is shown in U.S. Pat. Nos. 5,714,125 and 5,910,289, which are incorporated herein fully by this reference. The hub member is typically formed from a nontoxic plastic typically used for medical devices.

The forming step can be performed by any suitable process capable of roughening the outer surface of the cannula. Examples include (i) mechanical techniques such as grit blasting or contacting the outer surface with an abrasive medium; (ii) chemical techniques such as etching with an acid, and reacting the outer surface with an oxidant;

and/or (iii) thermal techniques such as heating the outer surface to a softening temperature followed by deformation of the softened area to form a corrugated surface and the like.

When grit blasting is employed to roughen the outer surface of the cannula, the preferred depth of the grit blast creates an outer diameter of the grit blasted (roughened) portion of the cannula that is slightly greater than the inner diameter of the hub bore. Typically, the outer diameter of the roughened portion is at least about 0.0001 inches, more typically at least about 0.0002 inches, and most typically at least about 0.0003 inches more than the smooth portion of the cannula. The outer diameter of the roughened portion is typically no more than about 0.001 inches and more typically no more than about 0.0008 inches more than the smooth portion of the cannula. The grit blasting is typically more circumferential than conventional grit blasting processes. Preferably, the roughened (enlarged) portion of the cannula extends at least about 320° C. around the circumference of the cannula.

In one configuration, the roughened portion of the cannula has a length and the cannula a total length. The length of the roughened portion is from about 25 to about 50% of the total length. The length of the roughened portion typically ranges from about 5 to about 50 mm and more typically from about 10 to about 25 mm. The length of the smooth portion typically ranges from about 0.25 to about 0.75 inches. The total length of the cannula typically ranges from about 0.5 to about 1 inches.

To provide a strong interference fit, the tolerance between the radii of the roughened and smooth portions on the one hand and of the hub bore on the other is typically relatively small. In one configuration, the radius of the smooth portion is at least about 5% and more typically at least about 10% less than the radius of the roughened portion. In yet another configuration, the radius of the hub bore ranges from about 75 to about 99% of the radius of the roughened portion and from about 100 to about 125% of the radius of the smooth portion.

It is preferred that the length of the roughened portion be substantially the same as the length of the hub bore. In one configuration, the length of the interface between the hub bore and the roughened portion ranges from about 50 to about 100% of a length of the roughened portion. In the configuration, the length of the roughened portion is preferably at least about 5 mm, more preferably at least about 7.5 mm, and even more preferably at least about 10 mm but not more than about 50 mm, more preferably not more than about 30 mm, and even more preferably not more than about 25 mm.

To further enhance the retention forces between the roughened portion and the adjoining hub bore, the hub in one configuration is made of an elastomeric material that elastically deforms (expands) when the roughened portion is forced into engagement with the inner wall of the bore. Preferably, the material has a flex modulus that is at least about 200,000 psi, more preferably at least about 225,000 psi, and even more preferably at least about 250,000 psi but no more than about 500,000 psi, more preferably no more than about 450,000 psi, and even more preferably no more than about 350,000 psi. Particularly preferred materials include plastics such as polycarbonate, polystyrene, polypropylene, and poly(vinyl chloride).

The manufacturing process of the present invention is not only capable of producing cannula assemblies inexpensively and at a high throughput but also satisfies the above-noted requirements for medical applications. The process can have a low incidence of damaging the point of the cannula due to the line-to-line engagement of the substantially smooth portion and the bore of the hub. Because the process does not utilize adhesives, the process cannot plug the hollow passageway extending the length of the cannula with adhesives. The process can be effective in holding lubricant coated needles and can provide a cannula assembly in which the minimum force required to push the cannula out of the hub is five pounds or more. Surprisingly, it has been discovered that the roughened portion of the cannula, elastic wall of the hub bore, and lubricant act synergistically to provide a relatively high pushout force for the cannula assembly.

In a second embodiment of the present invention, a medical device is provided that includes:

(a) a cannula having an exterior surface having a roughened portion and an unroughened portion; and (b) a hub member having an elastic bore, at least the roughened portion of the cannula being received in the elastic bore, wherein the bore has a radius such that an interference fit exists between the roughened surface of the cannula located in the bore and the surface of the bore.

In a third embodiment, a manufacturing method for a cannula assembly is provided that includes:

(a) grit blasting a portion of the cannula such that the grit blasted portion of the cannula's exterior surface is roughened relative to a non-grit blasted portion of the exterior surface that is substantially smooth;

(b) inserting the substantially smooth portion of the cannula into a bore of a hub member;

(c) forcing the substantially smooth portion to pass through the bore;

(d) inserting the grit blasted portion of the cannula into the hub bore; and (e) forcing at least most of the grit blasted portion of the cannula into an interference fit with the hub bore. In one configuration, the insertion force required to bring the roughened portion into full engagement with the hub bore is at least about 5 pounds and more typically at least about 7.5 pounds.

The foregoing list of embodiments is neither complete nor exhaustive. As will be obvious to one of ordinary skill in the art, a number of other embodiments are possible that include one or more of the above-noted features. Such embodiments are considered to be included within the scope of the present invention.

DETAILED DESCRIPTION

Figure 1:
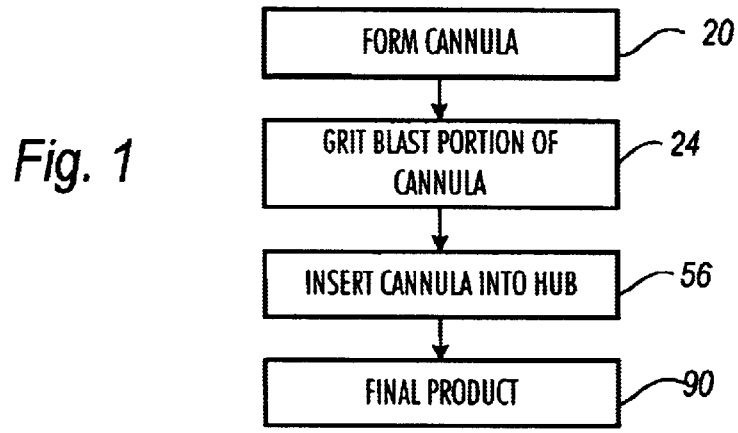
FIG. 1 is a flow schematic of an embodiment of a process according to the present invention.

The manufacturing process of the present invention will be described with reference to FIG. 1. In the first step 20, the cannula is formed by a suitable process. Such processes are conventional. Typically, the cannula is formed from a high strength, nontoxic material such as stainless steel. The cannula can be of any length or diameter, depending upon the application.

In the second step 24, the proximal (nonpuncturing or unpointed or blunt) end of the cannula is grit blasted to form a roughened surface or roughened portion of the cannula.

The depth of the grit blast is sufficiently high to permit a strong (nonadhesive) bond to form between the hub member and the cannula. Typically, the grit blast depth provides a radius for the roughened portion which creates an outer diameter greater than the inner diameter of the hub bore. However, the outer diameter of the roughened portion preferably is a diameter permissive for insertion into the hub bore (e.g., with an insertion force of no more than about 25 pounds).

Figure 2:
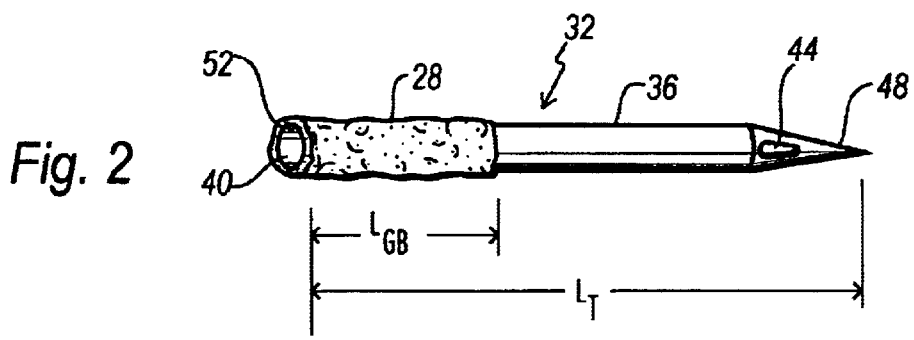
FIG. 2 is a perspective view of a cannula after the grit blasting.
Figure 3:
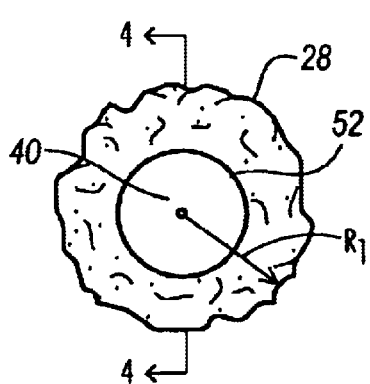
FIG. 3 is a rear view of the grit blasted cannula.
Figure 4:
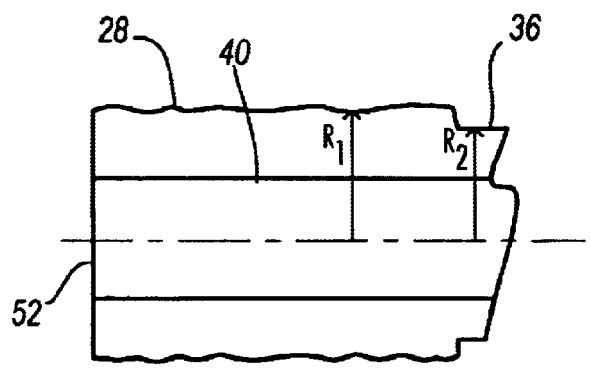
FIG. 4 is a cross-sectional view taken along line 4—4 of FIG. 3.
Figure 5:
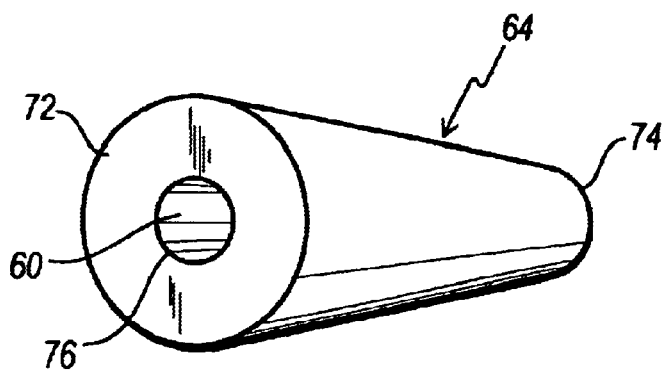
FIG. 5 is a perspective view of a hub member.
Figure 6:
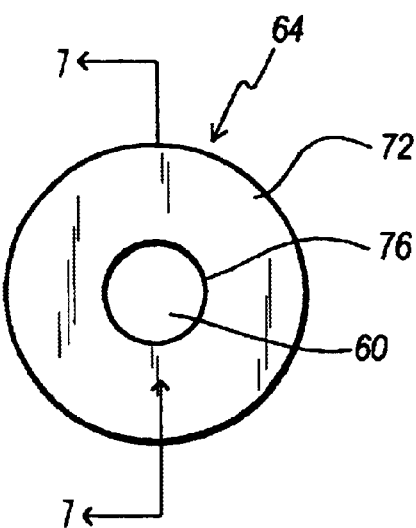
FIG. 6 is a rear view of the hub member.
Figure 7:
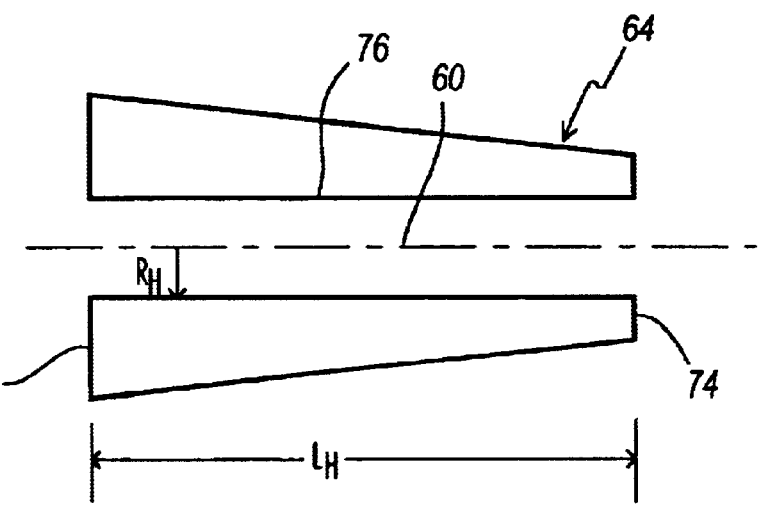
FIG. 7 is a cross-sectional view taken along line 7—7 of FIG. 6.
Figure 8:
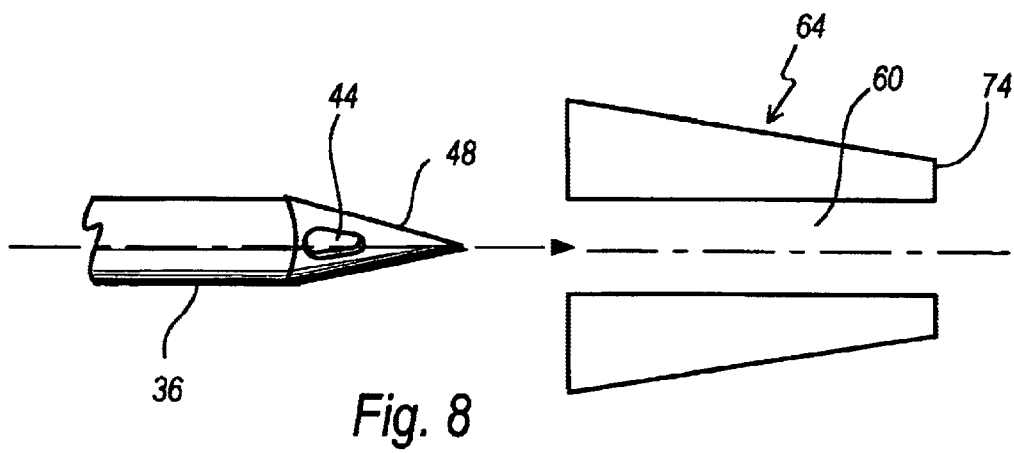
FIG. 8 is a view showing the cannula before insertion into the hub member bore, which is shown in the cross-sectional view of FIG. 7.
Figure 9:
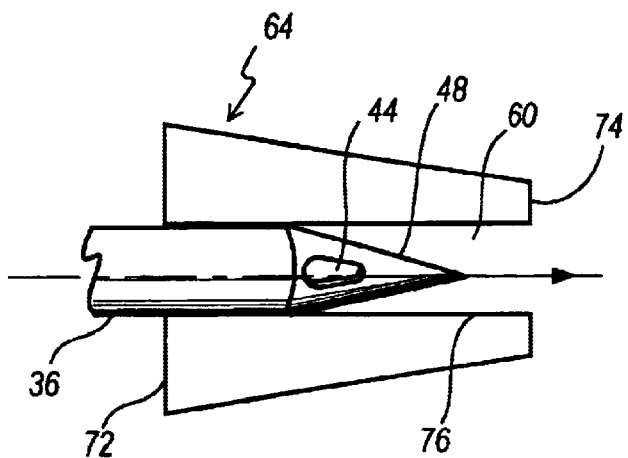
FIG. 9 is a view showing the substantially smooth portion of the cannula being inserted into the hub member bore, which is shown in the cross-sectional view of FIG. 7.
Figure 10:
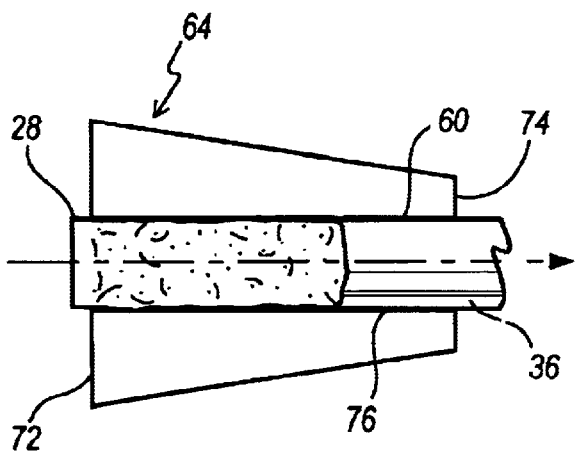
FIG. 10 is a view showing the roughened portion of the cannula being inserted into the hub member bore, which is shown in the cross-sectional view of FIG. 7.
Figure 11:
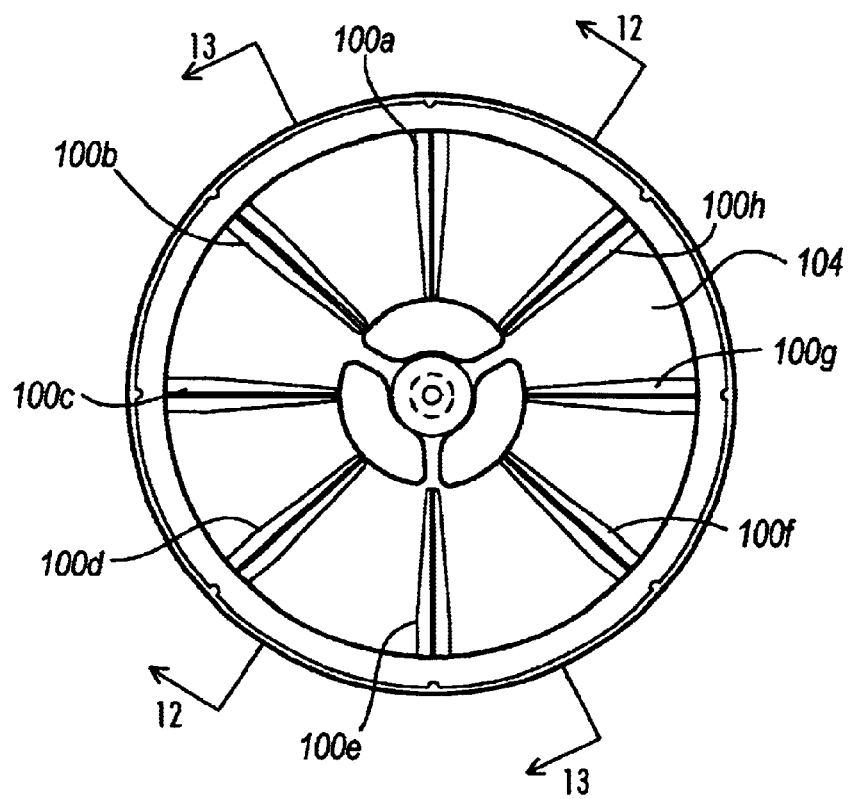
FIG. 11 is a plan view of a hub member according to another embodiment of the present invention.
Figure 12:
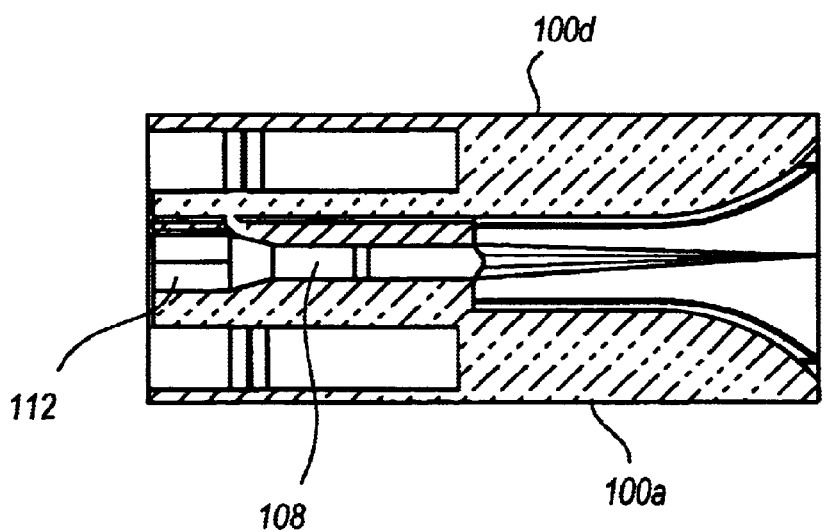
FIG. 12 is cross-sectional view of a hub member according to the embodiment of FIG. 11 with the cross-section being taken along line 12—12 of FIG. 11.
Figure 13:
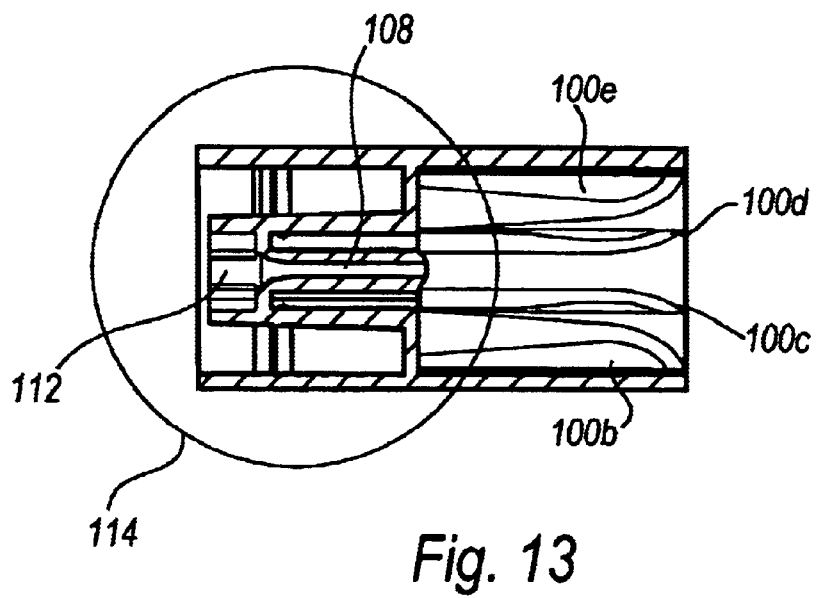
FIG. 13 is another cross-sectional view of the hub member of FIG. 11 with the cross-section being taken along line 13—13 of FIG. 11.
Figure 14:
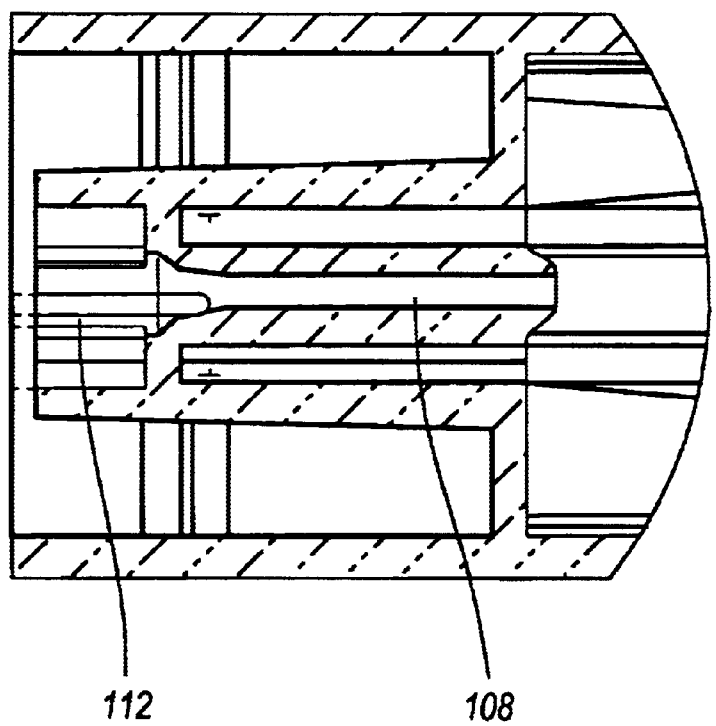
FIG. 14 is an enlarged view of the portion of the hub member in FIG. 13 enclosed by the circle 14.

Referring to FIGS. 2 through 4, the roughened surface 28 of the cannula 32 has a slightly larger outer radius ($R_1$) than the outer radius ($R_2$) of the substantially smooth portion 36 of the cannula. Typically, the (average, mean, median, and/or mode) radius $R_1$ is larger than $R_2$ and more typically ranges from about 2.5 to about 30% more than $R_2$, more typically from about 5 to about 30% more than $R_2$, and even more typically ranges from about 10 to about 25% more than $R_2$. Because of the irregular nature of the roughened surface 28, the radius $R_1$ will typically have slight fluctuations around the circumference of and along the length $L_{GB}$ of the roughened surface 28.

The length $L_{GB}$ of the roughened surface (FIG. 2) (and of the interface between the hub bore and the roughened surface) must be sufficient for the cannula to be firmly positioned in the hub member bore. Typically, the length $L_{GB}$ is from about 25 to about 75% and more typically from about 25 to about 50% of the total length L of the cannula. Typically, the length $L_{GB}$ ranges from about 0.25 to about 1 inch and more typically from about 0.5 to about 1 inch.

As will be appreciated, the cannula includes a central bore 40 that is in communication with one or more inlets 44 for passing fluids, such as bodily fluids down the length L of the cannula. The pointed end 48 is used to puncture a surface to permit fluids to pass through the inlet(s) 44, into the central bore 40, and through the outlet 52 into a collection vessel.

Referring again to FIG. 1 and to FIGS. 5 through 10, the cannula 32 is inserted in step 56 into a bore 60 of the hub member 64 and passed in the direction shown through the length of the bore 60 such that the roughened surface 28 engages the interior wall 76 of the bore 60. The cannula is inserted concentrically into the bore 60 at the rear 72 of the hub member 64 so that the substantially smooth portion 36 of the cannula 32 initially passes down the bore 60 in a line-to-line fit, and the roughened surface 28 subsequently engages the bore 60 in an interference (or friction) fit. The close tolerances between the radii of the surfaces 28 and 36 on the one hand and the bore wall 60 on the other prevents the cannula from digging too much into the bore wall 60. In this manner, the insertion force required to insert the cannula into the bore 60 is typically no more than about 25 pounds and more typically ranges from about 5 to about 20 pounds. As will be appreciated, the use of too strong an insertion force can bend or deform the cannula. The insertion force is typically less than the force required to dislodge the cannula from the cannula assembly.

The cylindrical outer surface of the portion 36 is substantially parallel to, concentric with, and in close tolerance with the cylindrical inner surface 76 of the bore 60. Typically, the radius $R_H$ of the bore 60 is substantially the same as the radius $R_2$ of the cannula portion 36 and more typically ranges from about 100 to about 125% of the radius $R_2$ and even more typically ranges from about 100 to about 120% of the radius $R_2$. In most applications, the radius $R_H$ ranges from about 0.5 to about 1.5 mm and even more typically from about 0.75 to about 1.25 mm.

The cylindrical outer surface of the surface 28 is also substantially parallel to, concentric with, and in close tolerance with the cylindrical inner surface 76 of the bore 60. Typically, the radius $R_H$ of the bore 60 is substantially less than (average, mean, median, and/or mode) the radius $R_1$ of the cannula portion 28 and more typically ranges from about 75 to about 99% of the (average, mean, median, and/or mode) radius $R_1$ and even more typically ranges from about 90 to about 99% of the radius (average, mean, median, and/or mode) $R_1$.

To provide adequate contact surface to form a strong (nonadhesive or nonfrictional) bond between the hub member 64 and the cannula 32, the length $L_{GB}$ (FIG. 2) of the roughened surface is typically close to the length $L_H$ (FIG. 7) of the hub bore (measured between the front 74 and rear 72 of the hub member). More typically, the bore length $L_H$ ranges from about 50 to about 150% of the length $L_{GB}$ and even more typically from about 75 to about 125% of the length $L_{GB}$.

Referring again to FIG. 1, the final product 90 has many desirable characteristics. The force required to remove the cannula from the hub member is typically more than required for functional use of the cannula assembly.

A hub member according to another embodiment is depicted in FIGS. 11–14. The hub member is of the type disclosed in U.S. Pat. Nos. 5,714,125 and 5,910,289. The hub member includes a number of inwardly facing ribs 100a–h radiating from a center 104. A hub bore 108 extends through a lower portion of the hub member body and opens into a drainage passage 112 located at a lower or proximal end of the hub member to facilitate drainage of fluids from the distal end of the hub member to the proximal end. At least most of the roughened portion of the cannula (not shown) engages the wall of the hub bore 108. The pointed end 48 of the cannula extends into the distal end of the hub member while the blunt end of the cannula is positioned in the drainage passage in the proximal end of the cannula. A flexible segment tube containing a bodily fluid such as blood is punctured by the pointed end of the cannula and the fluid in the tube flows through a passageway extending the length of the cannula and through the blunt end into a suitable receptacle. As noted, the interference fit between the roughened section of the cannula and the bore 108 is sufficient to eliminate the use of an adhesive to hold the cannula in the hub member, even while the cannula is being inserted into the flexible segment tube. The assembly is manufactured by inserting the pointed end 48 first into the drainage passage 112 and then into the bore 108 followed by the roughened portion until the roughened portion engages the bore wall. The ribs 100a–h restrict the lateral forces that are applied to the pointed end 48 of the cannula when a fluid-containing receptacle, such as a flexible segment tube containing a blood sample, is inserted into the distal end of the hub member for puncturing by the pointed end 48 and drainage through the drainage passage of the cannula.

The foregoing description of the present invention has been presented for purposes of illustration and description. Furthermore, the description is not intended to limit the invention to the form disclosed herein. Consequently, variations and modifications commensurate with the above teachings, in the skill or knowledge of the relevant art, are within the scope of the present invention. The embodiments described here and above are further intended to explain best modes for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A medical device, comprising:
   (a) a hypodermic needle having an exterior surface, with a roughened portion of the exterior surface being roughened and having a radius and a substantially smooth portion of the exterior surface being substantially smooth and having a radius; and
   (b) a hub member having a bore, at least the roughened portion of the needle being received in the bore, wherein the bore has a radius such that an interference fit exists between the exterior surface of the needle located in the bore and the surface of the bore and wherein the hub bore is substantially free of an adhesive.

2. The device of claim 1, wherein the roughened exterior surface extends substantially completely around a circumference of the needle.

3. The device of claim 2, wherein the bore has a length and the length of the bore is substantially the same as the length of the roughened portion.

4. The device of claim 1, wherein the roughened portion has a length and the needle a total length and the length of the roughened portion is from about 25 to about 50% of the total length.

5. The device of claim 1, wherein the hub is formed from an elastic material such that the central bore expands elastically when the roughened portion engages the wall of the central bore.

6. The device of claim 1, wherein the roughened portion has a radius and the radius is from about 2.5 to about 30% more than the radius of the substantially smooth portion.

7. The device of claim 1, wherein the hub member is formed from a material having a flex modulus ranging from about 200,000 psi to about 500,000 psi.

8. The device of claim 1, wherein the radius of the hub bore is from about 75 to about 99% of the second radius.

9. The device of claim 1, wherein the radius of the hub bore is from about 100 to about 125% of the radius of the substantially smooth portion of the needle.

10. The device of claim 1, wherein the radius of the roughened portion is at least about 0.0001 inches more than the radius of the hub bore.

11. The device of claim 1, wherein a length of an interface between the hub bore and roughened portion ranges from about 5 to about 50 mm.

12. The device of claim 1, wherein a length of the roughened portion ranges from about 5 to about 50 mm.

13. The device of claim 1, wherein the roughened portion has a length that ranges from about 5 to about 50 mm.

14. The device of claim 1, wherein the hub member possesses a plurality of ribs, said plurality of ribs extending from said hub bore such that said plurality of ribs lessen lateral forces applied to said needle.

15. A medical device, comprising:
   (a) a hypodermic needle having an exterior surface, with a roughened portion of the exterior surface being roughened and having a radius and a substantially smooth portion of the exterior surface being substantially smooth and having a radius; and
   (b) a hub member having a bore, at least the roughened portion of the needle being received in the bore, wherein the bore is substantially free of adhesive.

16. A medical device according to claim 15, wherein the bore has a radius such that an interference fit exists between the exterior surface of the needle located in the bore and the surface of the bore.

17. The device of claim 15, wherein the roughened exterior surface extends substantially completely around a circumference of the needle.

18. The device of claim 15, wherein the roughened portion has a length and the needle a total length and the length of the roughened portion is from about 25 to about 50% of the total length.

19. The device of claim 15, wherein the hub is formed from an elastic material such that the central bore expands elastically when the roughened portion engages the wall of the central bore.

20. The device of claim 15, wherein the roughened portion has a radius and the radius is from about 2.5 to about 30% more than the radius of the substantially smooth portion.

21. The device of claim 15, wherein the hub member is formed from a material having a flex modulus ranging from about 200,000 psi to about 500,000 psi.

22. The device of claim 15, wherein the radius of the hub bore is from about 75 to about 99% of the second radius.

23. The device of claim 15, the radius of the hub bore is from about 100 to about 125% of the radius of the substantially smooth portion of the needle.

24. The device of claim 15, wherein the radius of the roughened portion is at least about 0.0001 inches more than the radius of the hub bore.

25. The device of claim 15, wherein a length of an interface between the hub bore and roughened portion ranges from about 5 to about 50 mm.

26. The device of claim 15, wherein a length of the roughened portion ranges from about 5 to about 50 mm.

27. The device of claim 15, wherein the roughened portion has a length that ranges from about 5 to about 50 mm.

28. The device of claim 15, wherein the bore has a length and the length of the bore is substantially the same as the length of the roughened portion.

29. The device of claim 15, wherein the hub member possess a plurality of ribs, said plurality of ribs extending from said hub bore such that said plurality of ribs lessen lateral forces applied to said needle.

30. A medical device, comprising:
(a) a cannula having an exterior surface, with a roughened portion of the exterior surface being roughened and having a radius and a substantially smooth portion of the exterior surface being substantially smooth and having a radius; and
(b) a hub member having a bore, at least the roughened portion of the cannula being received in the bore, wherein the bore has a radius such that an interference fit exists between the exterior surface of the cannula located in the bore and the surface of the bore and wherein the roughened portion has a radius and the radius is from about 2.5 to about 30% more than the radius of the substantially smooth portion.

31. The device of claim 30, wherein the roughened exterior surface extends substantially completely around a circumference of the cannula and wherein the cannula is a hypodermic needle.

32. The device of claim 30, wherein the roughened portion has a length and the cannula a total length and the length of the roughened portion is from about 25 to about 50% of the total length.

33. The device of claim 30, wherein the hub is formed from an elastic material such that the central bore expands elastically when the roughened portion engages the wall of the central bore.

34. The device of claim 30, wherein the hub member is formed from a material having a flex modulus ranging from about 200,000 psi to about 500,000 psi.

35. The device of claim 30, wherein the radius of the hub bore is from about 75 to about 99% of the second radius.

36. The device of claim 30, wherein the radius of the hub bore is from about 100 to about 125% of the radius of the substantially smooth portion of the cannula.

37. The device of claim 30, wherein the radius of the roughened portion is at least about 0.0001 inches more than the radius of the hub bore.

38. The device of claim 30, wherein a length of an interface between the hub bore and roughened portion ranges from about 5 to about 50 mm.

39. The device of claim 30, wherein the hub bore is substantially free of an adhesive.

40. A medical device, comprising:
(a) a cannula having an exterior surface, with a roughened portion of the exterior surface being roughened and having a radius and a substantially smooth portion of the exterior surface being substantially smooth and having a radius; and
(b) a hub member having a bore, at least the roughened portion of the cannula being received in the bore, wherein the bore has a radius such that an interference fit exists between the exterior surface of the cannula located in the bore and the surface of the bore, wherein the hub member is formed from a material having a flex modulus ranging from about 200,000 psi to about 500,000 psi, and wherein the hub bore is substantially free of an adhesive.

41. The device of claim 40, wherein the roughened exterior surface extends substantially completely around a circumference of the cannula and wherein the cannula is a hypodermic needle.

42. The device of claim 40, wherein the roughened portion has a length and the cannula a total length and the length of the roughened portion is from about 25 to about 50% of the total length.

43. The device of claim 40, wherein the hub is formed from an elastic material such that the central bore expands elastically when the roughened portion engages the wall of the central bore.

44. The device of claim 40, wherein the roughened portion has a radius and the radius is from about 2.5 to about 30% more than the radius of the substantially smooth portion.

45. The device of claim 40, wherein the radius of the hub bore is from about 75 to about 99% of the second radius.

46. The device of claim 40, wherein the radius of the hub bore is from about 100 to about 125% of the radius of the substantially smooth portion of the cannula.

47. The device of claim 40, wherein the radius of the roughened portion is at least about 0.0001 inches more than the radius of the hub bore.

48. The device of claim 40, wherein a length of an interface between the hub bore and roughened portion ranges from about 5 to about 50 mm.

49. A medical device, comprising:
(a) a cannula having an exterior surface, with a roughened portion of the exterior surface being roughened and having a radius and a substantially smooth portion of the exterior surface being substantially smooth and having a radius; and
(b) a hub member having a bore, at least the roughened portion of the cannula being received in the bore, wherein the bore has a radius such that an interference fit exists between the exterior surface of the cannula located in the bore and the surface of the bore and wherein the radius of the hub bore is from about 75 to about 99% of the second radius.

50. The device of claim 49, wherein the roughened exterior surface extends substantially completely around a circumference of the cannula and wherein the cannula is a hypodermic needle.

51. The device of claim 49, wherein the roughened portion has a length and the cannula a total length and the length of the roughened portion is from about 25 to about 50% of the total length.

52. The device of claim 49, wherein the hub is formed from an elastic material such that the central bore expands elastically when the roughened portion engages the wall of the central bore.

53. The device of claim 49, wherein the roughened portion has a radius and the radius is from about 2.5 to about 30% more than the radius of the substantially smooth portion.

54. The device of claim 49, wherein the hub member is formed from a material having a flex modulus ranging from about 200,000 psi to about 500,000 psi.

55. The device of claim 49, the radius of the hub bore is from about 100 to about 125% of the radius of the substantially smooth portion of the cannula.

56. The device of claim 49, wherein the radius of the roughened portion is at least about 0.0001 inches more than the radius of the hub bore.

57. The device of claim 49, wherein a length of an interface between the hub bore and roughened portion ranges from about 5 to about 50 mm.

58. The device of claim 49, wherein the hub bore is substantially free of an adhesive.

59. A medical device, comprising:
(a) a cannula having an exterior surface, with a roughened portion of the exterior surface being roughened and having a radius and a substantially smooth portion of the exterior surface being substantially smooth and having a radius; and
(b) a hub member having a bore, at least the roughened portion of the cannula being received in the bore, wherein the bore has a radius such that an interference fit exists between the exterior surface of the cannula located in the bore and the surface of the bore, wherein the cannula is hypodermic needle, and wherein the radius of the hub bore is from about 100 to about 125% of the radius of the substantially smooth portion of the cannula.

60. The device claim 59, wherein the roughened exterior surface extends substantially completely around a circumference of the cannula.

61. The device of claim 59, wherein the roughened portion has a length and the cannula a total length and the length of the roughened portion is from about 25 to about 50% of the total length.

62. The device of claim 59, wherein the hub is formed from an elastic material such that the central bore expands elastically when the roughened portion engages the wall of the central bore.

63. The device of claim 59, wherein the roughened portion has a radius and the radius is from about 2.5 to about 30% more than the radius of the substantially smooth portion.

64. The device of claim 59, wherein the hub member is formed from a material having a flex modulus ranging from about 200,000 psi to about 500,000 psi.

65. The device of claim 59, wherein the radius of the hub bore is from about 75 to about 99% of the second radius.

66. The device of claim 59, wherein the radius of the roughened portion is at least about 0.0001 inches more than the radius of the hub bore.

67. The device of claim 59, wherein a length of an interface between the hub bore and roughened portion ranges from about 5 to about 50 mm.

68. The device of claim 59, wherein the hub bore is substantially free of an adhesive.

69. The device of claim 59, the hub member possesses a plurality of ribs, said plurality of ribs extending from said hub bore such that said plurality of ribs lessen lateral forces applied to said needle.

70. A medical device, comprising:
(a) a cannula having an exterior surface, with a roughened portion of the exterior surface being roughened and having a radius and a substantially smooth portion of the exterior surface being substantially smooth and having a radius; and
(b) a hub member having a bore, at least the roughened portion of the cannula being received in the bore, wherein the bore is substantially free of adhesive and wherein the roughened portion has a radius and the radius is from about 2.5 to about 30% more than the radius of the substantially smooth portion.

71. A medical device according to claim 70, wherein the bore has a radius such that an interference fit exists between the exterior surface of the cannula located in the bore and the surface of the bore and wherein the cannula is a hypodermic needle.

72. The device of claim 70, wherein the roughened exterior surface extends substantially completely around a circumference of the cannula and wherein the cannula is a needle.

73. The device of claim 70, wherein the roughened portion has a length and the cannula a total length and the length of the roughened portion is from about 25 to about 50% of the total length.

74. The device of claim 70, wherein the hub is formed from an elastic material such that the central bore expands elastically when the roughened portion engages the wall of the central bore.

75. The device of claim 70, wherein the hub member is formed from a material having a flex modulus ranging from about 200,000 psi to about 500,000 psi.

76. The device of claim 70, wherein the radius of the hub bore is from about 75 to about 99% of the second radius.

77. The device of claim 70, wherein the radius of the hub bore is from about 100 to about 125% of the radius of the substantially smooth portion of the cannula.

78. The device of claim 70, wherein the radius of the roughened portion is at least about 0.0001 inches more than the radius of the hub bore.

79. The device of claim 70, wherein a length of an interface between the hub bore and roughened portion ranges from about 5 to about 50 mm.

80. A medical device, comprising:
(a) a cannula having an exterior surface, with a roughened portion of the exterior surface being roughened and having a radius and a substantially smooth portion of the exterior surface being substantially smooth and having a radius; and
(b) a hub member having a bore, at least the roughened portion of the cannula being received in the bore, wherein the bore is substantially free of adhesive and wherein the hub member is formed from a material having a flex modulus ranging from about 200,000 psi to about 500,000 psi.

81. A medical device according to claim 80, wherein the bore has a radius such that an interference fit exists between the exterior surface of the cannula located in the bore and the surface of the bore and wherein the cannula is a hypodermic needle.

82. The device of claim 80, wherein the roughened exterior surface extends substantially completely around a circumference of the cannula and wherein the cannula is a needle.

83. The device of claim 80, wherein the roughened portion has a length and the cannula a total length and the length of the roughened portion is from about 25 to about 50% of the total length.

84. The device of claim 80, wherein the hub is formed from an elastic material such that the central bore expands elastically when the roughened portion engages the wall of the central bore.

85. The device of claim 80, wherein the roughened portion has a radius and the radius is from about 2.5 to about 30% more than the radius of the substantially smooth portion.

86. The device of claim 80, wherein the radius of the hub bore is from about 75 to about 99% of the second radius.

87. The device of claim 80, wherein the radius of the hub bore is from about 100 to about 125% of the radius of the substantially smooth portion of the cannula.

88. The device of claim 80, wherein the radius of the roughened portion is at least about 0.0001 inches more than the radius of the hub bore.

89. The device of claim 80, wherein a length of an interface between the hub bore and roughened portion ranges from about 5 to about 50 mm.

90. A medical device, comprising:
(a) a cannula having an exterior surface, with a roughened portion of the exterior surface being roughened and having a radius and a substantially smooth portion of the exterior surface being substantially smooth and having a radius; and
(b) a hub member having a bore, at least the roughened portion of the cannula being received in the bore, wherein the bore is substantially free of adhesive and wherein the radius of the hub bore is from about 75 to about 99% of the second radius.

91. A medical device according to claim 90, wherein the bore has a radius such that an interference fit exists between the exterior surface of the cannula located in the bore and the surface of the bore and wherein the cannula is a hypodermic needle.

92. The device of claim 90, wherein the roughened exterior surface extends substantially completely around a circumference of the cannula and wherein the cannula is a needle.

93. The device of claim 90, wherein the roughened portion has a length and the cannula a total length and the length of the roughened portion is from about 25 to about 50% of the total length.

94. The device of claim 90, wherein the hub is formed from an elastic material such that the central bore expands elastically when the roughened portion engage the wall of the central bore.

95. The device of claim 90, wherein the roughened portion has a radius and the radius is from about 2.5 to about 30% more than the radius of the substantially smooth portion.

96. The device of claim 90, wherein the hub member is formed from a material having a flex modulus ranging from about 200,000 psi to about 500,000 psi.

97. The device of claim 90, wherein the radius of the hub bore is from about 100 to about 125% of the radius of the substantially smooth portion of the cannula.

98. The device of claim 90, wherein the radius of the roughened portion is at least about 0.0001 inches more than the radius of the hub bore.

99. The device of claim 90, wherein a length of an interface between the hub bore and roughened portion ranges from about 5 to about 50 mm.

100. A medical device, comprising:
  (a) a cannula having an exterior surface, with a roughened portion of the exterior surface being roughened and having a radius and a substantially smooth portion of the exterior surface being substantially smooth and having a radius; and
  (b) a hub member having a bore, at least the roughened portion of the cannula being received in the bore, wherein the bore is substantially free of adhesive, wherein the cannula is a hypodermic needle, and wherein the radius of the hub bore is from about 100 to about 125% of the radius of the substantially smooth portion of the cannula.

101. A medical device according to claim 100, wherein the bore has a radius such that an interference fit exists between the exterior surface of the cannula located in the bore and the surface of the bore.

102. The device of claim 100, wherein the roughened exterior surface extends substantially completely around a circumference of the cannula.

103. The device of claim 100, wherein the roughened portion has a length and the cannula a total length and the length of the roughened portion is from about 25 to about 50% of the total length.

104. The device of claim 100, wherein the hub is formed from an elastic material such that the central bore expands elastically when the roughened portion engages the wall of the central bore.

105. The device of claim 100, wherein the roughened portion has a radius and the radius is from about 2.5 to about 30% more than the radius of the substantially smooth portion.

106. The device of claim 100, wherein the hub member is formed from a material having a flex modulus ranging from about 200,000 psi to about 500,000 psi.

107. The device of claim 100, wherein the radius of the hub bore is from about 75 to about 99% of the second radius.

108. The device of claim 100, wherein the radius of the roughened portion is at least about 0.0001 inches more than the radius of the hub bore.

109. The device of claim 100, wherein a length of an interface between the hub bore and roughened portion ranges from about 5 to about 50 mm.

110. A medical device, comprising:
  (a) a hypodermic needle having an exterior surface, with a roughened portion of the exterior surface being roughened and having a radius and a substantially smooth portion of the exterior surface being substantially smooth and having a radius; and
  (b) a hub member having a bore, at least the roughened portion of the needle being received in the bore, wherein the bore has a radius such that an interference fit exists between the exterior surface of the needle located in the bore and the surface of the bore wherein the radius of the roughened portion is at least about 0.0001 inches more than the radius of the hub bore.

111. A medical device, comprising:
  (a) a hypodermic needle having an exterior surface, with a roughened portion of the exterior surface being roughened and having a radius and a substantially smooth portion of the exterior surface being substantially smooth and having a radius; and
  (b) a hub member having a bore, at least the roughened portion of the needle being received in the bore, wherein the bore has a radius such that an interference fit exists between the exterior surface of the needle located in the bore and the surface of the bore, wherein the hub member possesses a plurality of ribs, said plurality of ribs extending from said hub bore such that said plurality of ribs lessen lateral forces applied to said needle.

112. A medical device, comprising:
  (a) a hypodermic needle having an exterior surface, with a roughened portion of the exterior surface being roughened and having a radius and a substantially smooth portion of the exterior surface being substantially smooth and having a radius; and
  (b) a hub member having a bore, at least the roughened portion of the needle being received in the bore, wherein the bore is substantially free of adhesive, wherein the radius of the roughened portion is at least about 0.0001 inches more than the radius of the hub bore.

113. A medical device, comprising:
  (a) a hypodermic needle having an exterior surface, with a roughened portion of the exterior surface being roughened and having a radius and a substantially smooth portion of the exterior surface being substantially smooth and having a radius; and
  (b) a hub member having a bore, at least the roughened portion of the needle being received in the bore, wherein the bore is substantially free of adhesive, wherein the radius of the roughened portion is at least about 0.0001 inches more than the radius of the hub bore, wherein the hub member possess a plurality of ribs, said plurality of ribs extending from said hub bore such that said plurality of ribs lessen lateral forces applied to said needle.

* * * * *

UNITED STATES PATENT AND TRADEMARK OFFICE
CERTIFICATE OF CORRECTION

PATENT NO. : 6,709,428 B2
DATED : March 23, 2004
INVENTOR(S) : Sagstetter

It is certified that error appears in the above-identified patent and that said Letters Patent is hereby corrected as shown below:

Column 2,
Line 48, after the word "and" and before the word "adjacent", please insert the word -- an --.

Column 3,
Line 19, please delete the "C." after the numeral "320.".

Column 7,
Line 64, please delete "second radius" and replace with -- radius of the roughened portion --.

Column 8,
Line 46, please delete "second radius" and replace with -- radius of the roughened portion --.

Column 10,
Line 29, please delete "second radius" and replace with -- radius of the roughened portion --.

Column 11,
Line 26, please delete "second radius" and replace with -- radius of the roughened portion --.

Column 12,
Lines 5 and 49, please delete "second radius" and replace with -- radius of the roughened portion --.

UNITED STATES PATENT AND TRADEMARK OFFICE
CERTIFICATE OF CORRECTION

PATENT NO.    : 6,709,428 B2
DATED         : March 23, 2004
INVENTOR(S)   : Sagstetter It is certified that error appears in the above-identified patent and that said Letters Patent is hereby corrected as shown below:

<u>Column 13,</u>
Line 2, please delete "second radius" and replace with -- radius of the roughened portion --.

Signed and Sealed this

Fifteenth Day of November, 2005

JON W. DUDAS
*Director of the United States Patent and Trademark Office*